(12) United States Patent
Tanaka

(10) Patent No.: US 7,360,326 B1
(45) Date of Patent: Apr. 22, 2008

(54) FLEXIBLE FOOTWEAR SOLE

(76) Inventor: John S. Tanaka, 68-1050 Mauna Lani Pt. Dr., Kohala Coast, HI (US) 96743

( * ) Notice: Subject to any disclaimer, the term of this patent is extended or adjusted under 35 U.S.C. 154(b) by 336 days.

(21) Appl. No.: 11/198,122

(22) Filed: Aug. 4, 2005

(51) Int. Cl.
*A61F 5/14* (2006.01)

(52) U.S. Cl. ........................................ 36/144

(58) Field of Classification Search ................ 36/25 R, 36/142, 143, 144
See application file for complete search history.

(56) References Cited

U.S. PATENT DOCUMENTS

| | | | | |
|---|---|---|---|---|
| 2,847,769 | A | * | 8/1958 | Schlesinger ................. 36/127 |
| 4,266,553 | A | | 5/1981 | Faiella |
| 4,682,425 | A | * | 7/1987 | Simmons ....................... 36/44 |
| 4,979,318 | A | * | 12/1990 | Cohen ............................ 36/43 |
| 5,036,604 | A | | 8/1991 | Rosen |
| 5,586,398 | A | * | 12/1996 | Carlson ....................... 36/144 |
| 6,226,901 | B1 | | 5/2001 | Rosen |
| 6,286,232 | B1 | | 9/2001 | Snyder et al. |
| 6,360,453 | B1 | | 3/2002 | Ellis, III |
| 6,604,301 | B1 | | 8/2003 | Manoli, II et al. |
| 2002/0139011 | A1 | * | 10/2002 | Kerrigan ...................... 36/144 |
| 2004/0040181 | A1 | * | 3/2004 | Kim ............................. 36/127 |
| 2005/0166423 | A1 | * | 8/2005 | Norton .......................... 36/28 |

* cited by examiner

*Primary Examiner*—Ted Kavanaugh
(74) *Attorney, Agent, or Firm*—Robert M. Hunter

(57) ABSTRACT

An item of footwear for a wearer, the item of footwear comprising a flexible sole structure that comprises a heel segment having horizontal upper and lower surfaces combined with other sole segments having arch (instep) and toe upper surfaces that are horizontal when unloaded, but that assume a negative upper surface slope when loaded, and with arch and toe lower surfaces that have a negative lower surface slope with unloaded, but that assume a horizontal position when loaded. In use, the item of footwear is operative to reduce the likelihood that a wearer having one of a variety of anatomical leg forms would fall outwardly (laterally) from his or her vertical plane.

7 Claims, 2 Drawing Sheets

FLEXIBLE FOOTWEAR SOLE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to a footwear sole assembly. In particular, the invention relates to a flexible footwear sole having a transverse sloped portion.

Footwear is as old as Man. Cave people used it to protect their soles. Progressively, the design of footwear became more specific. For walking comfort, sole designs that mimic the anatomical form of the feet, particularly at the arch, came into being. Other sole designs for various sports and running also came into being, all striving to protect and enhance the natural biomechanical function of ankle-to-foot movement. These designs have one constant: the bottom of the feet lies substantially horizontal, i.e., parallel to ground level.

For the purposes of this disclosure, the upper surface transverse angle, tilt, cant or slope of a portion of a sole of an item of footwear (e.g., a shoe, boot, slipper, etc.) is defined as positive when the top surface of the portion of the sole slopes down outwardly (laterally) and negative when the top surface of the portion of the sole slopes down inwardly (medially). The angle of the slope is expressed as a deviation from the horizontal in degrees. The horizontal is defined as substantially perpendicular to the vertical plane of the wearer of the item of footwear when the wearer is standing still on a horizontal surface and is balanced. This definition is consistent with that used in U.S. Pat. No. 5,036,603, except in this disclosure it applies to portions of the sole.

For the purposes of this disclosure, the lower surface transverse angle, tilt, cant or slope of a portion of a sole of an item of footwear (e.g., a shoe, boot, slipper, etc.) is defined as negative when the lower surface of the portion of the sole slopes down outwardly (laterally) and positive when the lower surface of the portion of sole slopes down inwardly (medially). The angle of the slope is expressed as a deviation from the horizontal in degrees. The horizontal is defined as substantially perpendicular to the vertical plane of the wearer of the item of footwear when the wearer is standing still on a horizontal surface and is balanced.

With advancing age, a person's sense of balance and leg muscle strength deteriorate. Lateral sway in the elderly increases while walking and corrective responses to this imbalance also suffer with age. These factors combine to increase the risk of falling with injurious consequences.

What would help the aged is a footwear structure having means to urge both knees medially towards the wearer's vertical plane that provides optimal balance when standing and walking. The footwear sole of the present invention provides such a structure. A footwear sole having an upper surface that, when loaded, assumes a negative slope in a narrow range of between two and six degrees is sufficient to allow a broad range of people with different anatomical legs forms to benefit from this invention.

The background art is characterized by U.S. Pat. Nos. 4,266,553; 5,036,604; 6,226,901; 6,286,232; 6,360,453; and 6,604,301; the disclosures of which patents are incorporated by reference as if fully set forth herein.

Faiella in U.S. Pat. No. 4,266,553 discloses a sole having a positive transverse slope (see his FIGS. 4, 5 and 6 which his FIG. 2 reveals are cross-sections of a right sole viewed from the back end of the sole). This is contrasted with applicant's invention which envisions a sole surface that assumes a negative transverse slope when loaded.

Rosen in U.S. Pat. No. 5,036,604 discloses an adjustable foot support system. This invention is limited in that the axial rotational transverse canting of the footbed must be adjusted.

Rosen in U.S. Pat. No. 6,226,901 B1 discloses an adjustable foot orthotic. This invention is limited it that adjustment of the transverse angular tilt or cant of the sole is necessary.

Snyder in U.S. Pat. No. 6,286,232 discloses an insole comprising a heel portion having a positive transverse slope. His FIG. 5 shows that his FIG. 9 is a cross-section viewed from the front end of the insole. This teaching is also documented in his specification at col. 6, lines 18-27. This is contrasted with applicant's invention which envisions a sole that assumes a negative transverse slope when loaded.

Ellis, III, in U.S. Pat. No. 6,360,453 discloses corrective shoe sole structures using a contour greater than the theoretically ideal stability plane. This invention is limited in that it teaches that both upper and lower sole surfaces must be substantially horizontal.

Manoli, II et al. in U.S. Pat. No. 6,604,301 disclose a shoe insert support. The Manoli, II et al. reference (U.S. Pat. No. 6,604,301) addresses a disorder termed "cavovarus foot" in which "the foot assumes a posture of an inward tipping of the heel (heel supination or varus, and a related forefoot pronation (forefoot valgus)." The heel portion 12 may have "a lateral heel wedge 13 formed therein to increase the valgus positioning of the heel." The elevation of the lateral aspect of only the forefoot 26 portion of the insert is an aspect of some embodiments of the Manoli, II et al. invention. This valgus wedge 28 decreases in elevation from the lateral to the medial aspect of the sole insert as shown in their FIGS. 4A and 4C. Their FIG. 3 shows that their FIGS. 4A and 4C are cross-sections of the forefoot portion viewed from the front end of the sole insert. This invention is limited in that providing for lateral flexing of the sole to produce a negative upper surface slope is not taught.

The background art does not teach a flexible sole structure that comprises a heel segment having horizontal upper and lower surfaces combined with other sole segments having arch (instep) and toe upper surfaces that are horizontal when unloaded, but that assume a negative upper surface slope when loaded, and with arch and toe lower surfaces that have a negative lower surface slope with unloaded, but that assume a horizontal position when loaded.

BRIEF SUMMARY OF THE INVENTION

The purpose of the invention is to minimize falls, particularly in the aged. One advantage of the invention is that it is very simple to fabricate. Another is that it is inexpensive.

One object of the invention is to aid an aged footwear wearer in standing and walking by urging his body mass inwardly (medially) towards his or her vertical plane. Another object is to reduce the likelihood of a wearer falling outwardly (laterally) from said plane.

In a preferred embodiment, the invention is an item of footwear for a wearer to use when walking on a walking surface, the item of footwear comprising: a flexible outer sole having a heel segment, an arch segment and a toe segment, said arch segment having an arch medial portion and an arch lateral portion, said toe segment having a toe medial portion and a toe lateral portion; said heel segment having a substantially uniform heel thickness; said arch lateral portion having an arch lateral portion thickness that is substantially the same as said heel thickness and said arch medial portion having an arch medial lower surface and an arch medial portion thickness that decreases medially; and said toe lateral portion having an toe lateral portion thickness that is substantially the same as said heel thickness and said toe medial portion having a toe medial portion thickness that decreases medially and a toe medial lower surface having a negative lower surface transverse slope of between two and six degrees when not in use; wherein said flexible outer sole is operative to flex when said wearer walks in said footwear to cause said arch medial lower surface and said toe medial lower surface to conform to said walking surface and said arch medial upper surface and said toe medial upper surface to assume a negative upper surface transverse slope of between two and six degrees when in use. Preferably, said lower surface transverse slope is about negative three degrees. Preferably, said toe lateral portion has a width of about one half inch. Preferably, said flexible outer sole is fabricated from a man-made material.

In another preferred embodiment, the invention further comprises: a mid sole; and an upper having an open toe and an open heel. Preferably, said upper is fabricated from leather. Preferably, said upper comprises a first strap portion and a second strap portion, said strap portions being fastenable with a hooks and loops fastener.

In yet another preferred embodiment, the invention is an upper sole for item of footwear for use on a walking surface comprising: a heel segment having a heel lower surface that when loaded is disposed substantially on the walking surface; a forward segment comprising a lateral portion having a lateral portion lower surface that is disposed substantially on the walking surface when loaded, and a medial portion having a medial portion lower surface that has a negative lower surface transverse slope when unloaded and that lies substantially on the walking surface when loaded.

In a further preferred embodiment, the invention is an item of footwear for a wearer to use on a walking surface, the item of footwear comprising: a flexible outer sole having a heel segment, an arch segment and a toe segment, said heel segment having a substantially uniform thickness, said arch segment having an arch medial portion and an arch lateral portion, said toe segment having a toe medial portion and a toe lateral portion; said heel segment having a heel upper surface and a heel lower surface that are disposed substantially parallel to the walking surface when the wearer's weight is supported by said heel segment; said toe lateral portion having a toe lateral portion upper surface and a toe lateral portion lower surface that are disposed substantially parallel to the walking surface when the wearer's weight is supported by said toe portion, said toe medial portion having a toe medial portion upper surface that has a negative upper surface slope when the wearer's weight is supported by said toe portion, and said toe medial portion having a toe medial portion lower surface having a negative lower surface slope when the wearer's weight is not supported by said toe portion; and said arch portion providing a transition between said heel segment and said toe segment.

In another preferred embodiment, the invention is an assembly within a shoe, boot or slipper for a wearer to use on a walking surface, the assembly comprising: a heel segment a heel segment comprising a heel cross section having a substantially constant thickness; a toe segment comprising a toe lateral portion cross section having a substantially constant thickness and a toe medial portion cross section having a thickness that decreases in the medial direction, an upper surface and a lower surface, said upper surface being disposed substantially parallel to the walking surface when the wearer's weight is not imposed on said toe segment and said upper surface being operative to assume an upper surface negative transverse slope when said wearer's weight is imposed on said toe segment; and an arch segment that provides a transition between said heel segment and said toe segment.

In yet another preferred embodiment, the invention is an assembly for use in walking or standing on a ground surface, said assembly comprising: a heel segment comprising a heel cross section having an upper heel surface that is disposed substantially parallel to said ground surface when loaded; a toe segment comprising a toe lateral portion having an upper toe lateral surface that is disposed substantially parallel to said ground surface when loaded and a toe medial portion cross section having a thickness that decreases in the medial direction; and an arch segment that provides a transition between said heel segment and said toe segment; wherein said toe medial portion has an toe medial portion upper surface that is disposed substantially parallel to said ground surface when unloaded and that flexes downward to substantially conform with said ground surface when loaded. In another preferred embodiment, the invention is a shoe, boot or slipper comprising one of the above assemblies.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate presently preferred embodiments of the invention. In the drawings.

Figure 1:
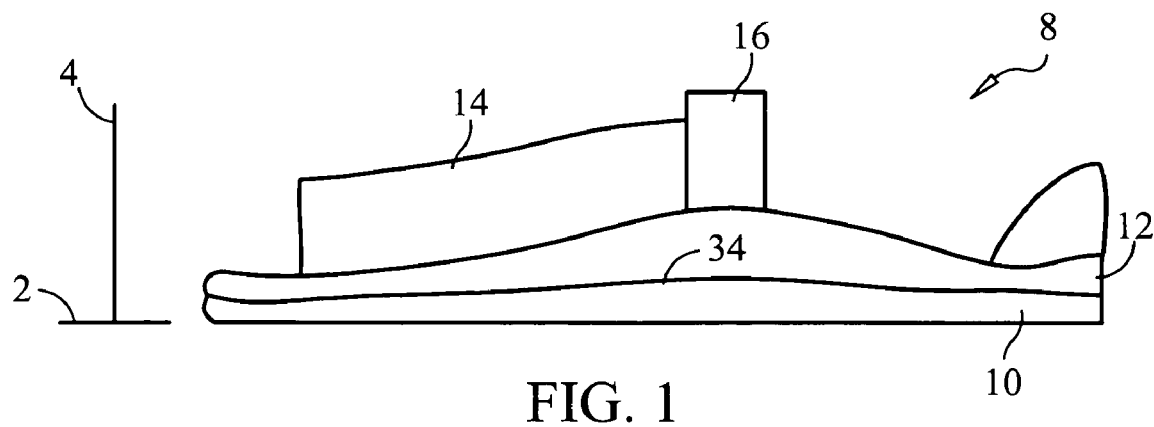
FIG. 1 is an elevation view of the medial side of a footwear item for a right foot in accordance with a preferred embodiment of the invention.

The following reference numerals are used to indicate the parts and environment of the invention on the drawings:
2 horizontal plane
4 vertical plane
8 slipper, slip on, item of foot wear
10 outer sole
12 mid sole
14 upper
16 strap
20 heel segment
22 arch segment; instep segment
24 toe segment
26 toe lateral portion
28 arch lateral portion
30 toe medial portion
32 arch medial portion
34 top surface
40 arch medial lower surface
42 arch lower surface transverse angle
44 toe medial lower surface
46 toe lower surface transverse angle
50 arch medial upper surface
52 arch upper surface transverse angle
54 toe medial upper surface
56 toe upper surface transverse angle

DETAILED DESCRIPTION OF THE INVENTION

In this description of a preferred embodiment of the invention, an item of footwear with straps to hold the item of footwear on the foot of the wearer is used as one example of an item of footwear to which the invention can be applied. An ordinary worker in the art will realize that the invention can be applied to all kinds of footwear, including slippers, sandals, shoes, boots, sports articles, etc. In the figures described herein, vertical plane 4 of the wearer is substantially perpendicular to horizontal plane 2 which is parallel to the ground upon which the wearer is standing or walking.

Referring to FIG. 1, a medial (inside) elevation view of right slipper 8 is shown, illustrating a preferred embodiment of the present invention that is appropriate for the right foot of a wearer. In this embodiment, slipper 8 comprises outer sole 10, mid sole 12 and upper 14. In a preferred embodiment, outer sole 10 is fabricated from a man-made (e.g., polymer) material and mid sole 12 and upper 14 are fabricated from leather. In a preferred embodiment, upper 12 comprises strap 16 that is provided with a hooks and loops fastener, e.g., Velcro® fastener. The left slipper (not shown) is preferably a mirror image of right slipper 8.

Figure 2:
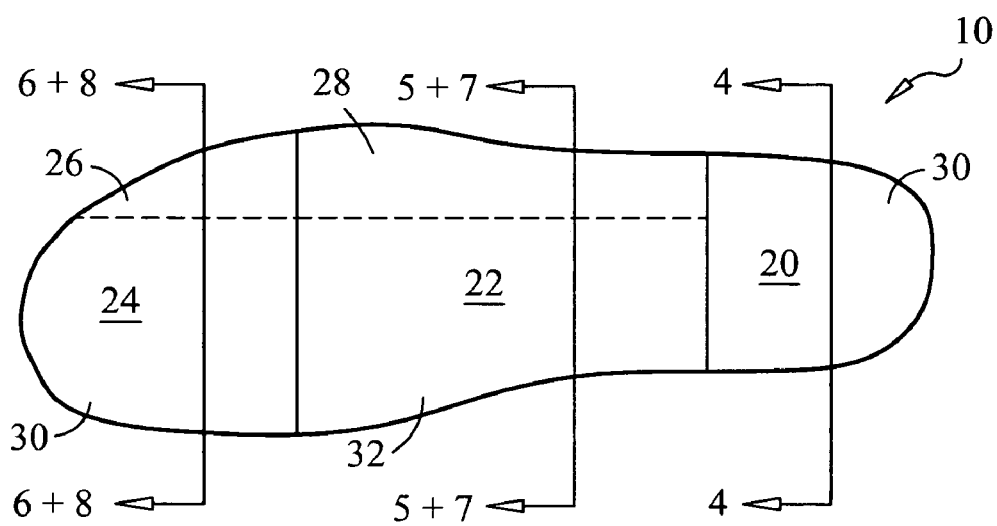
FIG. 2 is a plan (top) view of the outer sole of a preferred embodiment of the invention.
Figure 3:
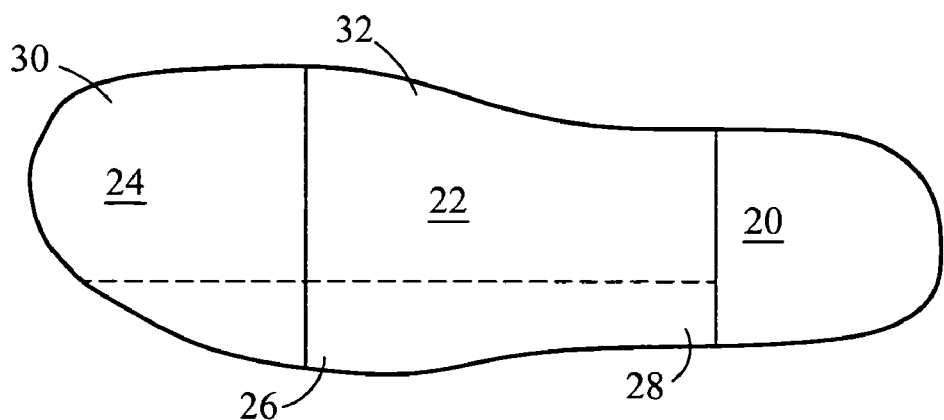
FIG. 3 is a plan (bottom) view of the outer sole of a preferred embodiment of the invention.

Referring to FIG. 2, a top view of the top of outer sole 10 of right slipper 8 is illustrated. Outer sole comprises heel segment 20, arch segment 22 and toe segment 24. Cross sections of outer sole 10 are presented in FIGS. 4 through 8. Referring to FIG. 3, a bottom view of the bottom of outer sole 10 of right slipper 8 is illustrated.

Figure 4:
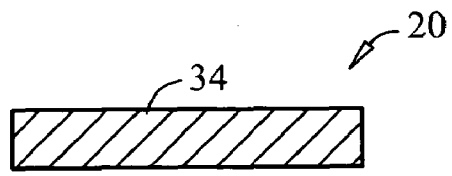
FIG. 4 is a cross-sectional view of the unloaded and loaded heel segment of the outer sole of a preferred embodiment of the invention.

Referring to FIG. 4, the same illustration is used to show heel segment 20 in an unloaded condition (without the wearer's weight being imposed on top surface 34) and in a loaded condition (without the wearer's weight being imposed on top surface 34). The use of the same illustration is possible because heel segment 20 does not bend in a transverse direction during use.

Figure 5:
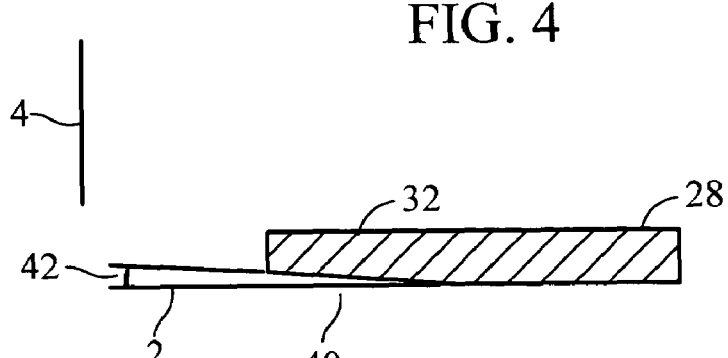
FIG. 5 is a cross-sectional view of the unloaded arch segment of the outer sole of a preferred embodiment of the invention.

Referring to FIG. 5, a cross section of arch segment 22 is shown in an unloaded condition (without the wearer's weight being imposed on top surface 34). In this condition, arch lateral portion 28 has a substantially uniform thickness, but arch medial portion 32 is progressively thinner in the medial direction because arch medial lower surface 40 has a negative lower surface transverse slope when unloaded. In a preferred embodiment, arch lower surface transverse angle 42 transitions from substantially zero adjacent at heel segment 20 to between two and six degrees adjacent to toe segment 24.

Figure 6:
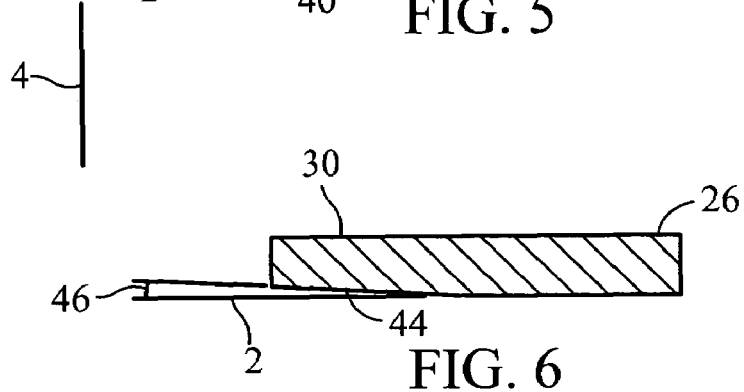
FIG. 6 is a cross-sectional view of the unloaded toe segment of the outer sole of a preferred embodiment of the invention.

Referring to FIG. 6, a cross section of toe segment 24 is shown in an unloaded condition (without the wearer's weight being imposed on top surface 34). In this condition, toe lateral portion 26 has a substantially uniform thickness, but toe medial portion 30 is progressively thinner in the medial direction because toe medial lower surface 44 has a negative lower surface transverse slope when unloaded. In a preferred embodiment, toe lower surface transverse angle 46 is between two and six degrees and is more preferably about three degrees.

Figure 7:
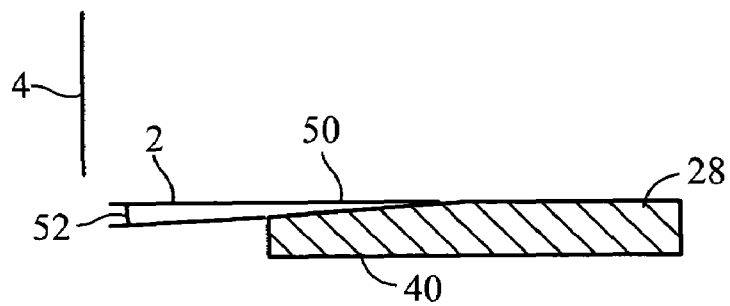
FIG. 7 is a cross-sectional view of the loaded arch segment of the outer sole of a preferred embodiment of the invention.

Referring to FIG. 7, a cross section of arch segment 22 is shown in a loaded condition (with the wearer's weight being imposed on top surface 34). In this condition, arch lateral portion 28 has a substantially uniform thickness, but arch medial portion 32 is progressively thinner in the medial direction and arch medial upper surface 50 flexes down to assume a negative upper surface transverse slope when loaded. In a preferred embodiment, arch upper surface transverse angle 52 is between two and six degrees and is more preferably about three degrees.

Figure 8:
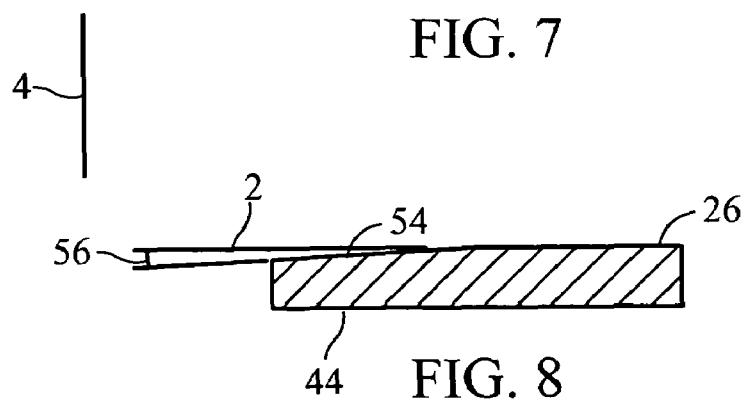
FIG. 8 is a cross-sectional view of the loaded toe segment of the outer sole of a preferred embodiment of the invention.

Referring to FIG. 8, a cross section of toe segment 24 is shown in a loaded condition (with the wearer's weight being imposed on top surface 34). In this condition, toe lateral portion 26 has a substantially uniform thickness, but toe medial portion 30 is progressively thinner in the medial direction and toe medial upper surface 54 flexes down to assume a negative upper surface transverse slope when loaded. In a preferred embodiment, toe upper surface transverse angle 56 between negative two and six degrees and is more preferably about three degrees.

In a preferred embodiment, each upper sole 10 is constructed of a cushion-free, lightweight material as thin as the transverse slope will allow. Preferably, top surface 34 is curvilinear to accept the contour of the foot, particularly at the arch and heel. In a preferred embodiment, sole 10 is fabricated of a compressible material to provide additional inward traction to the wearer.

Operation of the invention involves placing each item of footwear on a foot of the wearer. No adjustment is necessary. When the item of footwear is loaded, the negative slope of the upper surfaces of the slippers tends to urge both feet and knees anatomically inwardly towards vertical plane 4 when the wearer having different anatomical leg forms is standing or walking, thereby improving balance.

Many variations of the invention will occur to those skilled in the art. Some variations include providing a transverse tilt of negative about three to six degrees. Other variations call for providing a transverse tilt of negative about three degrees. All such variations are intended to be within the scope and spirit of the invention.

What is claimed is:

1. An item of footwear for a wearer to use when walking on a walking surface, the item of footwear comprising:
    a flexible outer sole having a heel segment, an arch segment and a toe segment, said arch segment having an arch medial portion and an arch lateral portion, said toe segment having a toe medial portion and a toe lateral portion;
    said heel segment having a substantially uniform heel thickness;

said arch lateral portion having an arch lateral portion thickness that is substantially the same as said heel thickness and said arch medial portion having an arch medial lower surface and an arch medial portion thickness that decreases medially; and said toe lateral portion having an toe lateral portion thickness that is substantially the same as said heel thickness and said toe medial portion having a toe medial portion thickness that decreases medially and a toe medial lower surface having a negative lower surface transverse slope of between two and six degrees when not in use;

wherein said flexible outer sole is operative to flex when said wearer walks in said footwear to cause said arch medial lower surface and said toe medial lower surface to conform to said walking surface and said arch medial upper surface and said toe medial upper surface to assume a negative upper surface transverse slope of between two and six degrees when in use.

2. The item of footwear of claim 1 wherein:
said lower surface transverse slope is about negative three degrees.

3. The item of footwear of claim 1 wherein:
said toe lateral portion has a width of about one half inch.

4. The item of footwear of claim 1 wherein:
said flexible outer sole is fabricated from a man-made material.

5. The item of footwear of claim 1 further comprising:
a mid sole; and
an upper having an open toe and an open heel.

6. The item of footwear of claim 5 wherein:
said upper is fabricated from leather.

7. The item of footwear of claim 5 wherein:
said upper comprises a first strap portion and a second strap portion, said strap portions being fastenable with a hooks and loops fastener.

* * * * *